United States Patent [19]
Elnagar

[11] Patent Number: 6,121,490
[45] Date of Patent: Sep. 19, 2000

[54] PRODUCTION OF SOLID TERTIARY AMINE OXIDES

[75] Inventor: Hassan Y. Elnagar, Baton Rouge, La.

[73] Assignee: Albemarle Corporation, Richmond, Va.

[21] Appl. No.: 09/291,164

[22] Filed: Apr. 14, 1999

[51] Int. Cl.$^7$ ................................................. C07C 292/02
[52] U.S. Cl. ........................... 564/298; 564/297; 564/301
[58] Field of Search ..................................... 564/298, 301, 564/297

[56] References Cited

U.S. PATENT DOCUMENTS

| | | | |
|---|---|---|---|
| 3,086,943 | 4/1963 | Lang | 252/152 |
| 3,215,741 | 11/1965 | Chadwick | 260/583 |
| 3,283,007 | 11/1966 | Chadwick | 260/583 |
| 3,332,999 | 7/1967 | Mitchell et al. | 260/583 |
| 3,333,000 | 7/1967 | Albert et al. | 260/583 |
| 3,432,555 | 3/1969 | Mahnken | 260/583 |
| 3,463,817 | 8/1969 | Mahnken | 260/583 |
| 3,776,959 | 12/1973 | Stalioraitis et al. | 260/583 D |
| 4,247,480 | 1/1981 | Murata et al. | 564/298 |
| 4,659,565 | 4/1987 | Smith et al. | 424/70 |
| 4,748,275 | 5/1988 | Smith et al. | 564/298 |
| 4,960,934 | 10/1990 | Smith et al. | 564/298 |
| 4,970,340 | 11/1990 | Smith | 564/298 |
| 5,055,232 | 10/1991 | Sauer et al. | 252/547 |
| 5,055,614 | 10/1991 | Sauer et al. | 564/298 |
| 5,075,501 | 12/1991 | Borland et al. | 564/297 |
| 5,082,940 | 1/1992 | Legrand et al. | 544/353 |
| 5,120,469 | 6/1992 | Smith et al. | 252/357 |
| 5,130,488 | 7/1992 | Smith et al. | 564/298 |
| 5,164,120 | 11/1992 | Borland et al. | 252/546 |
| 5,164,121 | 11/1992 | Smith et al. | 252/547 |
| 5,208,374 | 5/1993 | Borland et al. | 564/298 |
| 5,223,644 | 6/1993 | Blezard et al. | 564/2 |
| 5,292,954 | 3/1994 | Borland et al. | 564/298 |
| 5,442,113 | 8/1995 | Blezard et al. | 564/2 |
| 5,498,373 | 3/1996 | Miller et al. | 252/546 |
| 5,498,791 | 3/1996 | Blezard et al. | 564/2 |

FOREIGN PATENT DOCUMENTS 0307184  3/1989  European Pat. Off. .

OTHER PUBLICATIONS

WPIDS Abstract of JP 51032505, dated Mar. 19, 1976.
Caplus Abstract of JP 51032505, dated Mar. 19, 1976.
Hoh et al., "Hydrogen Peroxide Oxidation of Tertiary Amines", J. Am. Oil Chem. Soc., 1963, vol. 40, pp. 268–271.
Kirk–Othmer, "Encyclopedia of Chemical Technology" Third Edition, John Wiley & Sons, vol. 2, "Amine Oxides", 1978, pp. 259–271. (16 pages).

*Primary Examiner*—Samuel Barts
*Attorney, Agent, or Firm*—E. E. Spielman, Jr.

[57] ABSTRACT

A process for producing tertiary amine oxide having two methyl or ethyl groups and one long chain primary aliphatic group in a stable, solid form is described. Aqueous 65–90% hydrogen peroxide and tertiary amine having two methyl or ethyl groups and one primary aliphatic hydrocarbyl group of 8–24 carbon atoms are mixed in proportions of ca. 1.1–1.3 moles of hydrogen peroxide per mole of tertiary amine in the presence of carbon dioxide and in the absence of organic solvent. When the conversion of the tertiary amine to tertiary amine oxide in the reaction mass has reached ca. 60–90%, the reaction mass is transferred to a separate vessel and the reaction mass is then allowed to solidify at a temperature of ca. 20–60° C. The process makes possible the production of highly pure solid product without formation of any appreciable amounts of undesirable by-products. Also, the process is environmentally friendly, and the problems and expense associated with product workup, purification, crystallization, and waste product disposal are largely, if not entirely, avoided. Moreover, the solid storage stable products can be stored and shipped at significantly reduced costs as compared to liquid solutions. The products are useful in the manufacture of household and commercial laundry detergent formulations furnished in the form of powders or flakes.

10 Claims, No Drawings

PRODUCTION OF SOLID TERTIARY AMINE OXIDES

TECHNICAL FIELD

This invention relates to novel process technology for producing di-$C_{1-2}$ alkyl $C_{8-24}$ primary aliphatic hydrocarbyl tertiary amine oxides in stable, solid, non-hygroscopic form.

BACKGROUND

As pointed out in U.S. Pat. No. 4,970,340, trialkyl amine oxides can be made by reacting a trialkyl amine with aqueous hydrogen peroxide. They are useful for many purposes such as hair conditioners in shampoos as described in U.S. Pat. No. 3,086,943. When a $C_{10-16}$ alkyl dimethyl or ethyl alkyl amine oxide as described in U.S. Pat No. 3,086,943 is made, the product will gel if the concentration of the amine oxide exceeds about 30 weight percent. This results in a fairly dilute aqueous tert-amine oxide solution. When such solutions are shipped to remote locations as they usually are, the freight charges will be fairly high because of the large amount of water that is being shipped.

Alkyl dimethylamine oxides are described in Kirk-Othmer *Encyclopedia of Chemical Technology*, 3rd Ed. At page 266, Kirk-Othmer states that "when a strictly aqueous system is employed, final concentrations of amine oxide should be limited to below 35% since higher concentrations tend to gel and prevent good mixing."

Hoh et al., *J. Am. Oil Chem. Soc.*, 40 (1963) page 268–271 describe the synthesis of dimethyl dodecylamine oxide by reaction of dimethyl dodecylamine with 35% aqueous hydrogen peroxide. The product is a 30–40 weight percent aqueous solution of the amine oxide. Hoh et al. note that even using 35% aqueous hydrogen peroxide, the reaction mixture will gel unless diluted with water during the reaction.

Hoh et al. attempted to make dimethyl dodecylamine oxide without co-feeding water starting with 35%, 70% and 90% aqueous hydrogen peroxide. With 35% and 70% hydrogen peroxide, the product was a gel that could not be stirred. The reaction with 90% hydrogen peroxide was not completed because of darkening of the reaction mixture.

Chadwick U.S. Pat. No. 3,215,741 describes the preparation of di-$C_{1-2}$ alkyl $C_{10-20}$ alkyl amine oxides by reaction of the tert-amine with hydrogen peroxide. While attempting to make the desirable concentrated solutions of the amine oxide, Chadwick found that when commercially available hydrogen peroxide containing 20–90 weight percent $H_2O_2$ was used, the reaction sets up to a gel resembling a thick starch paste long before completion of the reaction. Chadwick's solution to the problem was to co-feed at least 20% hydrogen peroxide and sufficient water to the tert-amine such that the final product was water diluted. When dimethyl dodecylamine was used the most concentrated amine oxide solution that could be obtained was only 30–40 weight percent amine oxide.

Other disclosures in which relatively dilute aqueous solutions of tertiary amine oxides are formed include U.S. Pat. No. 4,247,480 wherein carbon dioxide is used as a reaction promoter, and EP 307 184 A2 published Mar. 15, 1989 wherein low temperature reactions in the presence of carbon dioxide are carried out in order to minimize nitrosamine formation in the product.

U.S. Pat. Nos. 4,970,340, 5,130,488, and 5,208,374, and JP 51/32505, published Mar. 19, 1976, describe processes in which concentrated aqueous solutions of tertiary amine oxides are formed via oxidation of specified tertiary amines with hydrogen peroxide.

U.S. Pat. No. 4,748,275 describes the discovery that solid non-hygroscopic flakeable di-$C_{14-30}$ alkyl $C_{1-2}$ alkylamine oxide is made by reacting di-$C_{14-30}$ alkyl $C_{1-2}$ alkylamine with aqueous hydrogen peroxide containing at least 40 weight percent $H_2O_2$ in the absence of a solvent. The solid product is recovered by crystallization at low temperature or by vacuum stripping of the solvent from the reaction product.

U.S. Pat. No. 5,075,501 describes non-hygroscopic solid tertiary amine oxide dihydrates useful in the preparation of dry detergent formulation such as laundry powders. These products are made by oxidizing certain mixed tertiary amines with aqueous hydrogen peroxide having a concentration of 50–90% by weight at 20–100° C. in the presence, at least during the latter part of the reaction, of an organic solvent in which the tertiary amine and the tertiary amine oxide are soluble at the reaction temperature but in which the tertiary amine oxide is insoluble at a lower temperature. In a comparative example it is shown in the patent that when no organic solvent (ethyl acetate) was used the reaction mixture formed a paste which cannot be fluidized even by increasing the temperature.

It would be of advantage if a way could be found for producing solid tertiary amine oxide products having two methyl and/or ethyl groups and one long chain primary aliphatic hydrocarbyl group without need for use of organic solvents, water dilution, low temperature crystallization procedures, or vacuum distillation operations. This invention is deemed to fulfill this objective in a highly efficient manner.

THE INVENTION

Pursuant to this invention there is provided a process for producing in solid form tertiary amine oxide having two methyl or ethyl groups and one long chain primary aliphatic group. This is accomplished by mixing (i) aqueous hydrogen peroxide solution containing about 65 to about 90 wt % of hydrogen peroxide, and (ii) tertiary amine having two methyl or ethyl groups and one primary aliphatic hydrocarbyl group of about 8 to about 24 carbon atoms, in proportions in the range of about 1.1 to about 1.3 moles of hydrogen peroxide per mole of tertiary amine, in the presence of carbon dioxide and in the absence of organic solvent such that tertiary amine in the reaction mass is being partially oxidized to tertiary amine oxide. When the conversion of the tertiary amine to tertiary amine oxide in the reaction mass has reached about 60 to about 90%, and preferably about 70 to about 90%, the fluid reaction mass is transferred to a separate vessel and the reaction mass is then allowed to solidify at a temperature in the range of about 20 to about 60° C. Most preferably, the transfer is carried out when the conversion of the tertiary amine to tertiary amine oxide in the reaction mass is in the range of about 80 to about 90%.

This invention makes possible the facile production of highly pure, solid, non-hygroscopic tertiary amine oxide dihydrates of the formula $(CH_3)_2RN\rightarrow O.(H_2O)_2$, where R is a primary linear or substantially linear aliphatic hydrocarbyl group having in the range of about 8 to about 24 carbon atoms, such as solid non-hygroscopic N,N-dimethyl-N-tetradecylamine oxide dihydrate. Since by virtue of this invention such products can now be formed in essentially quantitative yields by controlled oxidation of the requisite tertiary amine in a totally aqueous medium, the product tertiary amine oxide is highly pure and devoid of foul odor. Moreover, products such as N,N-dimethyl-N—$C_{8-24}$-alkylamine oxide dihydrates, when properly prepared pursuant to this invention, are stable and remain unchanged even after several years of storage under ambient temperature conditions.

The above and other embodiments and features of this invention will be still further apparent from the ensuing description and appended claims.

The amines that are used in the process of this invention are amines of the general formula $R^1R^2R^3N$, wherein each of $R^1$ and $R^2$ is, independently, a methyl or ethyl group, and wherein $R^3$ is a linear or substantially linear primary alkyl or alkenyl group which contains in the range of about 8 to about 24, and more preferably in the range of about 12 to about 16 carbon atoms. $R^3$ is preferably an alkyl group of this type. A few typical examples of such tertiary amines include dimethyl octyl amine, dimethyl nonyl amine, dimethyl decyl amine, dimethyl undecyl amine, dimethyl dodecyl amine, dimethyl tridecyl amine, dimethyl tetradecyl amine, dimethyl pentadecyl amine, dimethyl hexadecyl amine, dimethyl heptadecyl amine, dimethyl oxydecyl amine, dimethyl nonadecyl amine, dimethyl eicosyl amine, and the corresponding diethyl and methyl-ethyl compounds. Products in which the long chain hydrocarbyl group contains olefinic unsaturation include such compounds as dimethyl dodecenyl amine, dimethyl tetradecenyl amine, dimethyl hexadecenyl amine, and their long chain homologs. The substantially linear primary aliphatic hydrocarbyl tertiary amines that can be used will typically contain 1 or 2 branches that are no longer than 2 carbon atoms in length and are no closer to the nitrogen atom than the 3-position of the chain.

Concentrated aqueous solutions of hydrogen peroxide are utilized as the oxidizing agent in the practice of this invention. Thus the hydrogen peroxide as charged to the reaction will be about 65 to about 90 wt % aqueous hydrogen peroxide solutions. Preferred are aqueous solutions of hydrogen peroxide in the range of about 65 to about 75 wt %, with solutions of approximately 70 wt % being particularly preferred. The total amount of hydrogen peroxide used in the reaction should be at least the stoichiometric amount to theoretically convert the tertiary amine present to tertiary amine oxide. Preferably an excess of the aqueous hydrogen peroxide in the range of about 10 to about 30% will be employed. Most preferably the excess will be in the range of about 15 to about 20% over the stoichiometric amount.

The reaction is carried out in the presence of carbon dioxide. Typically, the reaction will be carried out in a reaction vessel under an atmosphere of carbon dioxide or in a reaction vessel into which carbon dioxide is introduced subsurface to the liquid in the reaction mixture. Other ways of providing the carbon dioxide can also be used, such as incremental additions of gaseous or solidified carbon dioxide to the reaction mass. The carbon dioxide serves as a reaction catalyst or reaction promoter. In this connection, the precise chemical make-up of the carbon dioxide-derived catalyst is not known with certainty. It may be that the carbon dioxide itself catalyzes or promotes the reaction. However, it is equally possible that the carbon dioxide reacts in situ to form either carbonic acid or peracid or some unidentified complex or other substance which serves as the actual catalytic entity. It will thus be understood that this invention is not limited to the particular form or chemical composition of the reaction catalyst or reaction promoter resulting from the introduction into the reaction mass of carbon dioxide as an ingredient.

Oxidation of the tertiary amine to the tertiary amine oxide is an exothermic reaction and will usually be performed by maintaining the reaction mixture at one or more temperatures within the range of about 40 to about 80° C. and preferably in the range of about 40 to about 60° C. To accomplish this it is preferable to add the concentrated aqueous hydrogen peroxide solution in increments to the tertiary amine, such addition being carried out as on a continuous feed basis or as a series of non-continuous additions, or as a combination of both such methods.

The foregoing reaction mass temperatures should be maintained at least during all or substantially all of the time incremental addition is taking place, and preferably such temperatures will be maintained during all or substantially all of the time the reaction is proceeding to the selected conversion in the range of about 60 to about 90%. Brief departures from the foregoing temperature ranges will usually not jeopardize the reaction provided that the reaction remains controllable. Thus ordinarily the reaction mixture will be maintained within at least one of the foregoing temperature ranges for at least 80% of the time between the initiation of the controlled oxidation and the point at which the selected 60–90% conversion has been reached and the reaction mass is transferred to another vessel for gradual total solidification. For best results, the reaction mass should be stirred or otherwise agitated during most, if not all, of the time between the initiation of the controlled oxidation and the point at which the selected 60–90% conversion has been reached and transfer of the reaction mass to a separate vessel is to be initiated.

The time during which concentrated aqueous hydrogen peroxide is introduced or added to the above specified tertiary amine will vary depending to some extent upon the rate of agitation of the reaction mass, and the scale of operation. In any event, this mixing of the two reactants should be slow enough to prevent the reaction from going out of control or reaching temperatures above about 80° C.

Another important feature of this invention noted above is that the reaction is performed in its entirety in the absence of any ancillary organic solvent. Moreover, the total amount of water present in the reaction mass is either (a) that which is furnished by the concentrated aqueous hydrogen peroxide being used or (b) that which is furnished by the concentrated aqueous hydrogen peroxide being used plus that which is added separately in order to theoretically dilute the concentrated aqueous hydrogen peroxide being fed to a lower concentration that would nevertheless still be at least about a 65 wt % aqueous solution (assuming no reaction was taking place). For example, if it is desired to feed 70 wt % aqueous hydrogen peroxide but only 80% wt % percent aqueous hydrogen peroxide is available, the 80 wt % solution could be fed along with a separate feed of that amount of water which would have diluted the 80 wt % solution to a 70 wt % solution. Alternatively, of course, the 80 wt % solution could first be diluted with the same amount of water to form a 70 wt % solution outside of the reactor and the resultant 70 wt % solution could then be fed to the reactor.

Most preferably no other component in addition to those specified above will be introduced into the reaction mixture. This enables the formation of a highly pure tertiary amine oxide product. However, it is possible, though less preferred, to use certain small amounts of a chelating agent such as ethylenediamine tetraacetic acid or a water-soluble salt thereof, diethylenetriamine pentaacetic acid or a water-soluble salt thereof, or S,S-ethylenediamine disuccinic acid or a water-soluble salt thereof. Other suitable chelating agents include nitrilotriacetic acid or a water-soluble salt thereof. The chelating agent, which serves as a sequestrant for metal ions which may be derived by extraction from metallic reactor walls, piping or the like, is preferably a metal-free chelating agent. In this way the chelating agent as added to the reaction mixture does not itself introduce any metal constituent(s). Thus if used as a salt, it is preferably an ammonium salt, although because of the small amounts of chelating agent used, alkali metal salts such as the sodium salts are acceptable for use. Typically, if used, the amount of chelating agent used will fall in the range of about 0.01 to about 0.1 wt %, and preferably in the range of about 0.05 to about 0.1 wt %, based on the total weight of the reaction mixture.

Of the chelating agents suitable for use, ethylenediamine tetraacetic acid, diethylenetriamine pentaacetic acid, and S,S-ethylenediamine disuccinic acid are the three most preferred materials.

Other permissible, though non-preferred components, which may be added to the reaction mass include additives to suppress nitrosamine formation, such as, for example, additives described in U.S. Pat. No. 5,223,644, 5,442,113 or 5,498,791.

Progress of the oxidation reaction is readily monitored by use of $^1$H-NMR inasmuch as the chemical and magnetic environment of the protons attached to the carbon atoms directly bonded to nitrogen are altered when the nitrogen atom is oxidized. Thus, unless and until all process details for a given operation have been standardized so that monitoring per se is unnecessary (times, temperatures, amounts, etc., providing the necessary controls without need for analysis), the progress of the reaction can be monitored by $^1$H-NMR to determine when the conversion of tertiary amine to tertiary amine oxide has reached the selected percentage of conversion between about 60 and about 90%. Once the reaction mixture reaches such selected percentage of conversion, the reaction mass, typically in the form of a slurry that can be manipulated and transferred without difficulty, is transferred to and allowed to solidify in predetermined shape such as a block, in a separate vessel. After transfer, the reaction mass is preferably allowed to stand in a quiescent state at one or more temperatures in the range of about 20 to about 60° C. until it completely solidifies. While the period for solidification will depend upon such factors as humidity, temperature and scale of operation, total solidification should usually occur within about 48 hours at ambient room temperature. At temperatures above room temperature, total solidification times are somewhat shorter.

It will be seen that this invention makes possible the production of a highly pure solid product without formation of any appreciable amounts of undesirable by-products. Thus not only is the present process technology environmentally friendly, but in addition problems and expense associated with product workup, purification, crystallization and waste product disposal are largely, if not entirely, avoided. Moreover, the solid storage stable products can be stored and shipped at significantly reduced costs as compared to liquid solutions. The products themselves can be used in the manufacture of household and commercial laundry detergent formulations furnished in the form of powders or flakes.

The following example is illustrative of a preferred way by which the this invention can be carried out. The example is not intended to limit, and should not be construed as limiting, the invention to the particular procedure described.

EXAMPLE 1

N,N-dimethyl-N-tetradecyl amine (ADMA®14 amine; Albemarle Corporation) (752 g, 3.12 mol) was charged into a 2-liter resin kettle and heated to 41° C. under $CO_2$ blanket before the heating source was removed. Hydrogen peroxide (142 mL, 70%, 3.74 mol) was added over 3.5 hours. The reaction mixture was monitored by $^1$H-NMR (see Table below). During peroxide addition, the reaction temperature ranged from 41 to 59° C. depending on the peroxide rate of addition. At the end of addition, the slurry was poured into an aluminum pan and was left to stand in a hood over the weekend, after which time $^1$H-NMR showed complete conversion of the N,N-dimethyl-N-tetradecyl amine to the corresponding oxide. The resulting N,N-dimethyl-N-tetradecyl amine oxide was obtained as snow-white solid block.

TABLE

| Time (min.) | Temp. (° C.) | $H_2O_2$ Added (mL) | Comments |
| --- | --- | --- | --- |
| 000 | 41 | 000 | start peroxide addition |
| 140 | 55 | 100 | 57% conversion (NMR), thick slurry |
| 169 | 55 | 118 (1.0 eq) | |
| 176 | 55 | 118 | 65% conversion |
| 204 | 59 | 142 (end) | 89% conversion, no foaming, poured the slurry into container |

Analysis of the product indicated that it contained 0.01 wt % amine, 12.9 wt % water, and 1.9 wt % peroxide. Thus, the reaction in Example 1 resulted in an essentially quantitatively yield of the desired amine oxide product.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process for producing in stable, solid form tertiary amine oxide having two methyl or ethyl groups and one long chain primary aliphatic group, which process comprises:

a) mixing (i) aqueous hydrogen peroxide solution containing about 65 to about 90 wt % of hydrogen peroxide, and (ii) tertiary amine having two methyl or ethyl groups and one primary aliphatic hydrocarbyl group of about 8 to about 24 carbon atoms in proportions in the range of about 1.1 to about 1.3 moles of hydrogen peroxide per mole of tertiary amine, in the presence of carbon dioxide and in the absence of organic solvent such that tertiary amine in the reaction mass is being oxidized to tertiary amine oxide, and b) when the conversion of the tertiary amine to tertiary amine oxide in the reaction mass has reached about 60 to about 90%, transferring the reaction mass to a separate vessel and allowing the reaction mass to solidify at a temperature in the range of about 20 to about 60° C.

2. A process according to claim 1 wherein the aqueous hydrogen peroxide is added in increments to the tertiary amine continuously and/or non-continuously, wherein the resultant mixture is agitated, and wherein the temperature of the reaction mass during all or substantially all of the time the oxidation reaction is taking place is maintained in the range of about 40 to about 80° C.

3. A process according to claim 1 wherein said tertiary amine has in the molecule two methyl groups and one linear or substantially linear saturated or olefinically-unsaturated aliphatic primary hydrocarbyl group.

4. A process according to claim 1 wherein the hydrogen peroxide being mixed with the amine is about 65 to about 75 wt % aqueous hydrogen peroxide.

5. A process according to claim 1 wherein said tertiary amine is at least one $C_{12-16}$ alkyldimethylamine in which the $C_{12-16}$ alkyl group is linear or substantially linear primary alkyl group, and wherein the hydrogen peroxide being mixed with the amine is about 65 to about 75 wt % aqueous hydrogen peroxide.

6. A process according to claim 1 wherein said tertiary amine is N,N-dimethyl-N-tetradecyl amine.

7. A process according to claim 1 wherein said tertiary amine has in the molecule two methyl groups and one linear or substantially linear saturated or olefinically-unsaturated aliphatic primary hydrocarbyl group, wherein the aqueous hydrogen peroxide mixed with the amine is about 65 to about 75 wt % aqueous hydrogen peroxide and is added in increments to the tertiary amine continuously and/or non-continuously, wherein the resultant mixture is agitated, wherein the temperature of the reaction mixture during all or substantially all of the time the oxidation is taking place is maintained in the range of about 40 to about 60° C.

8. A process according to claim 7 wherein said tertiary amine has in the molecule two methyl groups and one linear or substantially linear primary alkyl group.

9. A process according to claim 7 wherein said tertiary amine is at least one $C_{12-16}$ alkyldimethylamine in which the $C_{12-16}$ alkyl group is linear or substantially linear primary alkyl group.

10. A process according to claim 7 wherein said tertiary amine is N,N-dimethyl-N-tetradecyl amine.

* * * * *